US006297386B1

(12) United States Patent
Müller et al.

(10) Patent No.: US 6,297,386 B1
(45) Date of Patent: Oct. 2, 2001

(54) METHOD OF PREPARING 1-ALKYL-PYRAZOL-5-CARBOXYLIC ACID ESTERS

(75) Inventors: Nikolaus Müller, Monheim; Michael Matzke, Wuppertal, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/720,010

(22) PCT Filed: Jun. 21, 1999

(86) PCT No.: PCT/EP99/04297

§ 371 Date: Jan. 22, 2001

§ 102(e) Date: Jan. 22, 2001

(87) PCT Pub. No.: WO00/01673

PCT Pub. Date: Jan. 13, 2000

(30) Foreign Application Priority Data

Jul. 2, 1998 (DE) ............................. 198 29 616

(51) Int. Cl.[7] ................................. C07D 231/14
(52) U.S. Cl. ........................................ 548/374.1
(58) Field of Search ............................. 548/374.1

(56) References Cited

U.S. PATENT DOCUMENTS 5,977,378   11/1999   Müller et al. ............... 548/374.1

FOREIGN PATENT DOCUMENTS

| 1927429 | 12/1969 | (DE) . |
| 463756 | 1/1992 | (EP) . |
| 526004 | 2/1993 | (EP) . |
| 0854142 | 7/1998 | (EP) . |
| 1206088 | 9/1970 | (GB) . |
| 61040266 | 2/1986 | (JP) . |
| 2292263 | 12/1990 | (JP) . |
| 7118238 | 5/1995 | (JP) . |

OTHER PUBLICATIONS

J. Prakt. Chem. 12 (month unavailable) 1930, pp. 198–203, K. v. Auwers et al, "Über 1,3,4– und 1,4,5–Trimethyl–pyrazol".

Organikum, 19th edition (month unavailable) 1993, p. 490, "Allgemeine Arbeitsvorschrift für die Esterkondensation und die Glycidestersynthese nach Darzens".
Rompp Chemie Lexikon, 9th edition, vol. 5, pp. 3779–3780, "Raketentreibstoffe", Mar. 5, 2001, Corresponds to Version 1.3 of the CD–Rom–Römpp, Jürgen Falbe et al.
Chem. Ber., 59, Apr. 14, 1926, pp. 601–607, K. v. Auwers et al, Über die Isomerle–Verhältnisse in der Pyrazol–reihe, VI.: Über Alkylderivate der 8.5–Methyl–pyrazol–carbonsäure und des 3(5)–Methyl–pyrazols[1].
Chem. Ber 59 (month unavailable) 1926, pp. 1282–1302, K. v. Auwers et al, Über die Isomerie–Verhältnisse in der Pyrazol–Reihe, IX: Über 1.3–und 1.5–Dialkyl–pyrazole und verwandte Verbindungen.
*Database WPI, Section Ch, Week 199531, Derwent Publication Ltd., London, GB; Class B03, AN 1995–234200, XP002121095 & JP 07 118238 A (Ube Ind Ltd), May 9, 1995.
*Theilheimer W: "Synthetic Methods of Organic Chemistry. "Passage Text"", Synthetic Methods of Organic Chemistry. Bd. 16, 1962, Seite 204 XP002058626, Theilheimer W, N°428.
Aust. J. Chem, (month unavailable) 1983, 36, pp. 135–147, John L. Huppatz, "Systemic Fungicides. The Synthesis of Certain Pyrazole Analogues of Carboxin".
*Theilheimer W: "Synthetic Methods of Organic Chemistry, Passage", Synthetic Methods of Organic Chemistry, Bd. 2, 1975, Seite 128 XP002058628, Theilheimer W, N°368.
*Theilheimer W: "Synthetic Methods of Organic Chemistry", Synthetic Methods of Organic Chemistry, Bd. 6, Seite 148 XP002058629, Theilheimer W, N°403.
*Database WPI, Section Ch, Week 198615, Derwent Publications Ltd., London, GB; Class B03, AN 1986–096631, XP002121094 & JP 61 040266 A(Morishita Pharm Co. Ltd), Feb. 26, 1986.

Primary Examiner—Robert W. Ramsuer
(74) Attorney, Agent, or Firm—Joseph C. Gil; Richard E. L. Henderson

(57) ABSTRACT

The invention relates to the preparation of 1-alkyl-pyrazole-5-carboxylic esters by reacting the enolate of a 2,4-diketocarboxylic ester in the presence of a solvent and water with an N-alkylhydrazinium salt. This process permits a particularly economical preparation of 1-alkyl-pyrazole-5-carboxylic esters in a simple manner and with only limited formation of undesirable isomers.

13 Claims, No Drawings

METHOD OF PREPARING 1-ALKYL-PYRAZOL-5-CARBOXYLIC ACID ESTERS

This application is a 371 of PCT/EP99/042 97 filed Jun. 21, 1999.

The present invention relates to a process for preparing 1-alkyl-, in particular also 1,3-dialkyl-pyrazole-5-carboxylic esters, from the enolate of 2,4-dicarboxylic esters and N-alkylhydrazinium salts.

It is already known to prepare 1-alkyl-pyrazole-5-carboxylic esters by alkylation of pyrazole-3-carboxylic esters with alkylating agents (for example alkyl halides, dialkyl sulfates or alkyl tosylates).

Thus, EP Published Specification 463 756 and EP Published Specification 526 004 describe the preparation of ethyl 1-methyl-3-n-propyl-pyrazole-5-carboxylate by reaction of ethyl 3-n-propyl-pyrazole-5-carboxylate with dimethyl sulfate. Apparently, a mixture is formed here comprising the two isomeric N-methyl-pyrazoles, requiring complicated separation by means of chromatographic methods.

The preparation of ethyl 1-methyl- and ethyl 1-ethyl-3-propyl-pyrazole-5-carboxylate from ethyl 3-propyl-pyrazole-5-carboxylate by alkylation with dimethyl sulfate or triethyloxonium tetrafluoroborate is described in DE Published Specification 19 27 429. No statements are made with respect to the possible occurrence of isomers, their separation or the total yield of the desired product, even though, based on the literature which was then known, the formation of isomer mixtures had always to be considered a possibility. Thus, methylation of methyl 3,4-dimethyl-pyrazole-5-carboxylate with methyl iodide and sodium methoxide as auxiliary base leads to a mixture of the isomeric trimethyl pyrazole carboxylic esters which could be separated into the isomers only "after repeated rectification" (J. Prakt. Chem. 126, 198 (1930)). The ethylation of ethyl 3-methylpyrazole-5-carboxylate with ethyl bromide/sodium in absolute alcohol gives a mixture of ethyl 1-ethyl-3-methyl-pyrazole-5-carboxylate and ethyl 1-ethyl-5-methyl-pyrazole-3-carboxylate in a ratio of approximately 1:3, i.e. the frequently desired 1,3-dialkyl isomer is formed in considerably smaller amounts and is obtained pure only after three-fold distillation (Chem. Ber. 59, 603 (1926)).

The other, frequently used method of preparing 1-alkyl-pyrazole-5-carboxylic esters comprises the reaction of 2,4-diketocarboxylic esters with N-alkylhydrazines. Likewise, isomer mixtures are obtained here which generally contain predominantly the frequently undesirable isomer, which then again necessitates a complicated separation process. Thus, the reaction of ethyl 2,4-dioxopentanecarboxylate with methyl hydrazine gives a 1:1 mixture of 1,5-dimethyl-pyrazole-3-carboxylate and the corresponding 2,4-dimethyl isomer (Austr. J. Chem. 36, 135–147 (1983)). Other authors report even more unfavorable ratios of 35:65 (Chem. Ber. 59, 1282 (1926)), which were confirmed in comparative laboratory experiments, for this reaction. The same authors obtained even worse results (isomer ratio 15:85) with analogous etherified enols, for example with O-ethyl acetone oxalate and methylhydrazine. In general, either the free hydrazines with the diketo ester, or the sodium salt of the diketo ester (enolate) and hydrazine salts, from which the hydrazine is liberated with bases such as sodium hydroxide or sodium carbonate, are employed for these reactions.

The reaction mixtures which are obtained in the preparation processes of the prior art cannot be worked up by distillation, because they contain by-products which prevent distillative separation of the two isomers formed.

According to an earlier proposal by the Applicant, 1-alkyl-pyrazole-5-carboxylic esters are prepared by reacting the enolate of a 2,4-diketocarboxylic ester in the presence of a solvent, for example an alcohol, with an N-alkylhydrazinium salt (German Patent Application 19 701 277.9). The N-alkylhydrazinium salt has to be prepared from alkylhydrazine using an acid in the presence of alcohol. To this end, alkylhydrazines have to be handled in pure form which, owing to their toxicity and explosive properties (see Römpp Lexikon Chemie—Version 1.3 (1997)—methylhydrazine is a rocket fuel), is only possible with a particularly high expenditure for safety.

There is therefore still a need for a process for the selective preparation of 1-alkyl-pyrazole-5-carboxylic esters which are as free as possible from isomers, which process does not require such a high expenditure for safety.

This invention, accordingly, provides a process for preparing 1-alkyl-pyrazole-5-carboxylic esters of the formula (I)

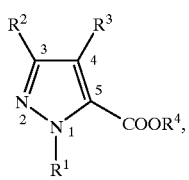

(I)

in which $R^1$ and $R^4$ independently of one another each represent straight-chain or branched $C_1$–$C_6$-alkyl, $C_3$–$C_7$-cycloalkyl or optionally substituted $C_7$–$C_{12}$-aralkyl and $R^2$ and $R^3$ independently of one another each represent hydrogen, straight-chain or branched $C_1$–$C_6$-alkyl, $C_3$–$C_7$-cycloalkyl or optionally substituted $C_7$–$C_{12}$-aralkyl, which comprises reacting the enolate of a 2,4-diketocarboxylic ester of the formula

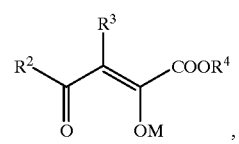

(II)

in which $R^2$, $R^3$ and $R^4$ are each as defined in formula (I) and

M represents the equivalent of a metal atom, in the presence of a solvent and of water with an N-alkylhydrazinium salt of the formula (III)

$R^1$—$NH_2$—$NH_2^\oplus$ $^{R5}COO^\ominus$ (III), in which $R^1$ is as defined in formula (I) and $R^5$ together with the $COO^\ominus$ moiety represents the anion of an organic acid.

$C_7$–$C_{12}$-aralkyl, preferably benzyl, and $C_6$–$C_{10}$-aryl (mentioned hereinbelow), preferably phenyl (mentioned hereinbelow), may in each case contain, for example, up to two substituents from the group of the halogen atoms and the $C_1$–$C_4$-alkyl radicals.

Preferred diketocarboxylic ester enolates of the formula (II) are those where the radicals $R^2$ and $R^3$ independently of one another each represent hydrogen, straight-chain or branched $C_1$–$C_4$-alkyl, $C_3$–$C_6$-cycloalkyl or optionally substituted benzyl, and also those where the radical $R^4$ represents straight-chain or branched $C_1$–$C_4$-alkyl.

Particular preference is given to 2,4-diketocarboxylic ester enolates of the formula (II) where $R^2$ and $R^4$ each represent $C_1$–$C_4$-alkyl and $R^3$ represents H.

In the formula (II), M preferably represents a monovalent metal atom or an equivalent of a divalent metal atom. Examples are lithium, sodium, potassium, calcium and magnesium. Particular preference is given to sodium, lithium and magnesium.

Preferred N-alkylhydrazinium salts of the formula (III) are those where $R^1$ represents straight-chain or branched $C_1$–$C_4$-alkyl or optionally substituted benzyl and $R^5$ represents straight-chain or branched $C_1$–$C_6$-alkyl, $C_3$–$C_7$-cycloalkyl, $C_7$–$C_{12}$-aralkyl or $C_6$–$C_{10}$-aryl, which may optionally be substituted as mentioned above.

$R^5$ together with the $COO^\ominus$ moiety may also represent an anion of a polybasic organic acid. Examples are anions of oxalic, malonic, succinic, glutaric, adipic, maleic, fumaric, malic, tartaric and citric acid, and they may in each case be mono- or polyanions. Such anions may contain one or more $COO^\ominus$ moieties and, if appropriate, additionally also COOH radicals. In the case of anions of polybasic organic acids, the alkylhydrazine can be employed in equimolar amounts, based on the acid, or in amounts which correspond to the number of the acid groups.

The diketo ester enolate of the formula (II) can be prepared, for example, from the corresponding pure isolated 2,4-diketo esters by addition of an alkoxide. Suitable alkoxides are, for example, those which correspond to the formula (IV)

 (IV), in which
M is as defined for formula (II),
$R^6$ represents $C_1$–$C_4$-alkyl and
n corresponds to the valency of M.

The preparation of the diketo ester enolates of the formula (II) can be carried out in a solvent, for example in a $C_1$–$C_4$-alcohol.

Diketo ester enolates of the formula (II) can also be prepared according to the customary methods by condensation of a methyl alkyl ketone of the formula (V)

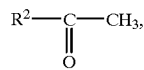 (V)

in which
$R^2$ is as defined for formula (I),
with an oxalic ester of the formula $R^4OOC$—$COOR^4$ (VI)

in which
$R^4$ is as defined for formula (I). This reaction is likewise carried out in the presence of an alkoxide, for example an alkoxide of the formula (IV), and a solvent. The resulting crude reaction mixture can be employed directly in the reaction with the N-alkylhydrazinium salt of the formula (III).

Suitable solvents for the reaction of the methyl alkyl ketones of the formula (V) with the oxalic esters of the formula (VI) and further reaction with the N-alkylhydrazinium salts of the formula (III) are, for example, alcohols such as methanol, ethanol, isopropanol, n-propanol and n-, i-, s- and t-butanol. The alkoxide of the formula (IV) can be prepared by dissolving an alkali metal or alkaline earth metal M in the alcohol which corresponds to the alkoxide of the formula (IV).

Water is advantageously introduced into the reaction mixture together with the hydrazinium salt of the formula (III), or subsequently thereto.

The hydrazinium salt of the formula (III) can be prepared, for example, by mixing an alkylhydrazine of the formula (VII)

 (VII), in which
$R^1$ is as defined in formula (I),
with a carboxylic acid of the formula (VIII)

 (VIII), in which
$R^5$ is as defined in formula (III).

If appropriate, the reaction can be carried out with addition of a solvent, for example an alcohol.

The reaction is preferably carried out by using a solution of hydrazinium salts of the formula (III), which was obtained by reacting an aqueous solution of an alkylhydrazine (for example of the formula (VII)) with a carboxylic acid (for example of the formula (VIII)). In this manner, the handling of pure alkylhydrazines can be avoided and the high expenditure for safety which is required for handling pure alkylhydrazines can be dispensed with. In this manner, the 1-alkyl-pyrazole-5-carboxylic esters can be prepared considerably more economically.

To prepare compounds of the formula (I), the enolate of formula (II) and the N-alkylhydrazinium salt of the formula (III), both advantageously in the form of the alcoholic or aqueous solution which is obtained on their preparation, are admixed. Those proportions of the enolates or the N-alkylhydrazinium salts which may tend to precipitate can be dissolved again or kept in solution by heating and/or addition of more solvent and/or water. For example, an alcoholic enolate solution may be added to an aqueous N-alkylhydrazinium salt solution which was initially charged or, vice versa, an aqueous N-alkylhydrazinium salt solution may be added to an alcoholic enolate solution which was initially charged.

The total amounts of solvent and water employed are generally chosen so that stirrable suspensions or solutions are present. The total amount of solvent plus water per mole of reaction mixture may, for example, be between 100 and 2000 ml. This amount is preferably from 200 to 1000 ml, particularly preferably from 250 to 500 ml. The total amount of solvent plus water may comprise, for example, from 10 to 60% by weight, preferably from 15 to 40% by weight, of water.

The molar ratio for the reaction of the diketo ester enolates of the formula (II) with the N-alkylhydrazinium salts of the formula (III) may vary within wide limits, and is, for example, from 5:1 to 1:5. In a preferred embodiment, approximately equimolar amounts of diketo ester enolate of the formula (II) and N-alkylhydrazinium salt of the formula (III) are reacted, for example from 0.9 to 1.1 mol of diketo ester enolate of the formula (II) per mole of N-alkylhydrazinium salt of the formula (III).

The amount of alkoxide for the preparation of the diketo ester enolate may also vary within wide limits. It is preferably at least equimolar.

If the diketo ester is prepared in a previous step as described above from a ketone of the formula (V) and an oxalic ester of the formula (VI), their molar ratios may also vary. The reaction is preferably carried out with slightly less, for example in each case from 1 to 10 mol % less, of the ketone of the formula (V), based on the oxalic ester of the formula (VI) and the alkoxide of the formula (IV). The two last mentioned compounds are preferably employed in approximately the same molar amount as the respective other compound. The molar ratios are then, for example, from 0.9 to 0.99 mol of ketone of the formula (V) to from 0.9 to 1.1 mol of oxalic ester of the formula (VI) to from 0.9 to 1.1 mol of alkoxide of the formula (IV).

When preparing the N-alkylhydrazinium salt of the formula (III) from an alkylhydrazine of the formula (VII), preferably an aqueous solution of an alkylhydrazine of the formula (III), and a carboxylic acid of the formula (VIII), the molar ratio of the two materials charged can also vary within wide limits. Preference is given to using an amount of from 1 to 1.5 mol of acid per mole of alkylhydrazine. Particular preference is given to using equimolar amounts of alkylhydrazine and carboxylic acid.

An excess of carboxylic acid of the formula (VIII) is advantageous when the alkoxide of the formula (IV) is present in excess. This alkoxide excess can then be neutralized with the excess of acid.

The reaction temperatures for the reaction of the reaction components of the formula (II) and (III) may, for example, be between −20 and +100° C., preferably between 0 and 80° C., particularly preferably between 20 and 50° C. This also applies to the temperatures when stirring is continued after the reaction components have been admixed.

The reaction times (mixing of the reaction components + stirring of the reaction mixture after the reaction components have been admixed) may, for example, be between 0.5 and 12 hours, preferably between 1 and 8 hours, particularly preferably between 2 and 5 hours. Preference is given to using the following compounds of the formula (II) for the process according to the invention:

Ethyl 2,4-diketopentanecarboxylate as sodium, lithium, potassium or magnesium enolate, ethyl 2,4-diketohexanecarboxylate, ethyl 2,4-diketoheptanecarboxylate, ethyl 2,4-diketooctanecarboxylate and ethyl 2,4-diketo-3-ethylpentanecarboxylate (in each case in the form of their sodium, lithium, magnesium or potassium enolate salts) and methyl, n-propyl, i-propyl and n-, i-, s- and t-butyl esters of the abovementioned diketocarboxylic acids, likewise in the form of the abovementioned enolate salts.

Preferred N-alkylhydrazinium salts of the formula (III) are methylhydrazinium formate, acetate, propionate, butyrate, isobutyrate, benzoate, oxalate and succinate, N-propylhydrazinium formate, acetate, propionate, butyrate, isobutyrate and benzoate, ethylhydrazinium formate, acetate, propionate, butyrate, i-butyrate, benzoate, oxalate and succinate and also the hydrazinium salts of i-propyl-, n-butyl-, t-butyl-, benzyl- and N-pentylhydrazine with the abovementioned carboxylic acid anions.

A general embodiment of the process according to the invention, illustrated using the example of the reaction of ethyl 2,4-diketoheptanecarboxylate sodium salt with methylhydrazinium formate, is as follows:

The sodium salt of ethyl 2,4-diketoheptanecarboxylate is prepared similarly to known procedures (see, for example Organikum, 19th Ed. p. 490 (1993)) from 2-pentanone and oxalic ester in ethanol, using sodium ethoxide as auxiliary base. This solution is kept at 50° C. to prevent precipitation of the enolate and added over a period of one hour to a solution of methylhydrazinium formate in water which had been prepared earlier (methylhydrazine is initially charged in water, acetic acid is added dropwise). Stirring is continued for an appropriate period of time, excess ethanol is distilled off and the mixture is admixed with toluene and, if appropriate, more water. To improve phase separation, it is possible to add, if appropriate a suitable surfactant, for example an alkanesulfonate, and/or to increase the ion concentration in the aqueous phase, for example by addition of a salt. The toluene phase is separated off, the aqueous phase is extracted two more times with toluene and the combined organic phases are reextracted with water. The water may, if appropriate, contain an acid and/or a salt. The solution of the crude pyrazole in toluene is concentrated by distilling off the solvent, and the residue is subjected to fractional distillation under reduced pressure. The two isomeric pyrazoles can be isolated in pure form without any great expenditure for separation.

It is extremely surprising that even in the presence of water the use of the N-alkylhydrazinium salts for the preparation of N-alkylpyrazoles has a favorable effect on the regioselectivity. According to the prior art, the undesired isomer having the alkyl radical at the nitrogen which is further away from the carboxyl group is preferably formed when free alkylhydrazines (whether used as such or liberated from their salts by aqueous alkali metal solutions is immaterial) are used, whereas the use of N-alkylhydrazinium salts of the formula (III) preferably affords the desired isomer (I) where the alkyl group is located at the nitrogen which is closest to the carbonyl group in the pyrazole. Surprisingly, the expenditure for the handling of pure alkylhydrazine can be avoided by the presence of water according to the invention, and the desired isomer is nevertheless obtained in high amounts.

1-Alkyl-pyrazole-5-carboxylic esters of formula (1) are useful intermediates for preparing pharmaceutically active compounds with vasoactive and/or spasmolytic action (see EP Published Specification 463 756, EP Published Specification 526 004 and DE Published Specification 19 27 429), and also for preparing pesticides having insecticidal and acaricidal action (see JP Published Specification 89–114 466).

EXAMPLE

Ethyl 1-methyl-3-n-propylpyrazole-5-carboxylate

In a 1 l four-necked flask, 146.1 g of diethyl oxalate were initially charged and 86.1 g of pentan-2-one and 3 g of ethanol were added. With stirring, 340.3 g of a 20% strength by weight solution of sodium ethoxide were metered in at 25–40° C. over a period of 1 hour, and the addition funnel was subsequently rinsed with 3 g of ethanol. The reaction mixture was stirred at 50° C. for 1 hour and subsequently at 80° C. for 1 hour and subsequently cooled to 50° C. While the reaction mixture was stirred, 126.7 g of a 40% strength by weight aqueous solution of methylhydrazine were initially charged in another flask, 66 g of acetic acid were added dropwise to this at 5–30° C. over a period of 1 hour and the mixture was subsequently cooled to 0° C. The solution of ethyl 2,4-diketoheptanoate enolate prepared above, which had been kept at 50° C., was added dropwise over a period of 2 hours to this mixture in such a manner that the temperature of the reaction mixture was kept between 0 and 10° C. and the temperature of the ethyl 2,4-diketoheptanoate enolate solution was kept at approximately 50° C. The addition funnel was rinsed with 3 g of ethanol. Solvent was subsequently distilled off until a bottom temperature of 88° C. was reached. The bottom was cooled and mixed with stirring with 300 ml of toluene, 500 ml of water, 45 g of Mersolat® H 30 and 20 g of sodium chloride. The aqueous phase was separated off and washed with 100 ml of toluene. The organic phases were combined, washed with 210 g of 10% strength by weight sulfuric acid and 200 ml of 10% strength by weight sodium chloride solution and subsequently concentrated at 60 mbar until a bottom temperature of 70° C. was reached. This gave 211 g of a brown oil which was composed of 54.2% by weight of ethyl 1-methyl-3-n-propylpyrazole-5-carboxylate and 19.5% by weight of the "wrong isomer" ethyl 1-methyl-5-n-propylpyrazole-3-carboxylate, which corresponds to a crude yield of 58.3% of the desired compound.

What is claimed is:

1. A process for preparing 1-alkyl-pyrazole-5-carboxylic esters of the formula (I)

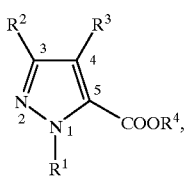

(I)

wherein
$R^1$ and $R^4$ independently of one another each represent straight-chain or branched $C_1-C_6$-alkyl, $C_3-C_7$-cycloalkyl or optionally substituted $C_7-C_{12}$-aralkyl and $R^2$ and $R^3$ independently represent hydrogen, straight-chain or branched $C_1-C_6$-alkyl, $C_3-C_7$-cycloalkyl, or optionally substituted $C_7-C_{12}$-aralkyl, comprising reacting
(1) the enolate of a 2,4-diketocarboxylic ester of the formula (II)

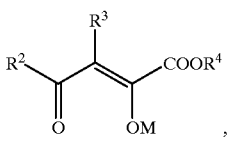

(II)

wherein
$R^2$, $R^3$, and $R^4$ are each as defined for formula (I) and
M represents the equivalent of a metal atom, with
(2) an N-alkylhydrazinium salt of the formula (III)

(III), wherein
$R^1$ is as defined in formula (I) and
$R^5$ together with the $COO^\ominus$ moiety represents the anion of an organic acid, in the presence of a solvent and water, wherein the total amount of solvent plus water comprises from 10 to 60% by weight of water.

2. The process as claimed in claim 1 wherein in the diketocarboxylic ester enolate of the formula (II), $R^2$ and $R^3$ independently of one another each represent hydrogen, straight-chain or branched $C_1-C_4$-alkyl, $C_3-C_6$-cycloalkyl, or optionally substituted benzyl; $R^4$ represents straight-chain or branched $C_1-C_4$-alkyl; and M represents lithium, sodium, potassium, calcium, or magnesium.

3. The process as claimed in claim 1 wherein in the N-alkylhydrazinium salt of the formula (III), $R^1$ represents straight-chain or branched $C_1-C_4$-alkyl or optionally substituted benzyl and $R^5$ represents straight-chain or branched $C_1-C_6$-alkyl, $C_3-C_7$-cycloalkyl, optionally substituted $C_7-C_{12}$-aralkyl, or optionally substituted $C_6-C_{10}$-aryl.

4. The process as claimed in claim 1 wherein in formula (III), $R^5$ together with the $COO^\ominus$ moiety represents an anion of a polybasic organic acid.

5. The process as claimed in claim 4 wherein the polybasic organic acid is oxalic, malonic, succinic, glutaric, adipic, maleic, fumaric, malic, tartaric, or citric acid.

6. The process as claimed in claim 1 wherein water is introduced into the reaction mixture together with the N-alkylhydrazinium salt of the formula (III) or subsequently thereto.

7. The process as claimed in claim 1 wherein the N-alkylhydrazinium salt of the formula (III) is used as a solution obtained by reaction of an aqueous solution of an alkylhydrazine with a carboxylic acid.

8. The process as claimed in claim 1 wherein the diketo ester enolate of formula (II) is prepared from the corresponding pure isolated 2,4-diketo ester by addition of an alkoxide to the 2,4-diketo ester in the presence of a solvent.

9. The process as claimed in claim 8 wherein the amount of alkoxide is at least equimolar relative to the 2,4-diketo ester.

10. The process as claimed in claim 1 wherein 100 to 2000 ml of solvent or water are present per mole of reaction mixture.

11. The process as claimed in claim 1 wherein the molar ratio of the diketo ester enolate of the formula (II) with the N-alkylhydrazinium salt of the formula (III) is between 5:1 and 1:5.

12. The process as claimed in claim 1 wherein the diketo ester enolate of formula (II)

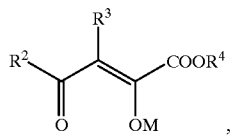

(II)

wherein
$R^2$ and $R^4$ each represent $C_1-C_4$-alkyl,
$R^3$ represents H, and
M represents the equivalent of a metal atom, is prepared by reacting a methyl alkyl ketone of formula (V)

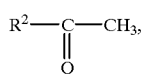

(V)

wherein $R^2$ is as defined for formula (II) with an oxalic ester of the formula (VI)

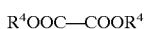

(VI), wherein $R^4$ is as defined for formula (II), in the presence of an alkoxide of the formula (IV)

(IV), wherein
$R^6$ represents $C_1-C_4$-alkyl,
M is as defined for formula (II), and
n corresponds to the valency of M,
wherein the molar ratios are from 0.9 to 0.99 mol of the methyl alkyl ketone of formula (V) to from 0.9 to 1.1 mol of the oxalic ester of the formula (VI) to from 0.9 to 1.1 mol of the alkoxide of the formula (IV).

13. The process as claimed in claim 1 wherein the reaction temperature is between −20 and +100° C. and the reaction times are between 0.5 and 12 hours.

* * * * *